United States Patent [19]

Sato et al.

[11] 4,208,268
[45] Jun. 17, 1980

[54] METHOD OF PROCESSING THERMAL CRACKED BY-PRODUCT OIL

[75] Inventors: Atsushi Sato; Isoo Shimizu, both of Yokohama; Eiichi Matsuzaka, Tokyo, all of Japan

[73] Assignee: Nippon Petrochemicals Company, Limited, Tokyo, Japan

[21] Appl. No.: 890,302

[22] Filed: Mar. 27, 1978

[30] Foreign Application Priority Data

Mar. 29, 1977 [JP] Japan .................. 52-33942

[51] Int. Cl.$^2$ .................. C10G 17/00; C10G 29/00
[52] U.S. Cl. ............................... 208/46; 208/71; 208/256; 208/257; 585/25; 585/422
[58] Field of Search .................. 208/46, 71, 256, 257; 260/668 B; 485/25, 422

[56] References Cited

U.S. PATENT DOCUMENTS

| | | | |
|---|---|---|---|
| 2,387,237 | 10/1945 | Ault | 208/46 |
| 2,415,541 | 2/1947 | Soday | 208/46 |
| 3,844,931 | 10/1974 | Ishiguro et al. | 208/46 |

Primary Examiner—Herbert Levine
Attorney, Agent, or Firm—Scully, Scott, Murphy & Presser

[57] ABSTRACT

This invention provides a method of processing thermal cracked by-product oil which comprises reacting a distillate from a thermal cracked by-product oil principally containing components of a boiling range between 75° C. and 198° C. said distillate being one of the distillates from the cracking of petroleum hydrocarbons at a cracking temperature of 700° C. or higher, and containing a ratio of 5-100 molar percent aromatic olefins to non-olefinic aromatic hydrocarbons, in liquid phase in the presence of an acid catalyst under such conditions that the reaction temperature is 0° C.–200° C., the liquid residence time is 0.1 hour–5 hours and wherein the content of aromatic olefins in the reaction system are 5% by weight or less at the end of the reaction, to yield a processed distillate containing non-condensed di- and tricyclic aromatic compounds which are reaction products of aromatic olefins with other aromatic hydrocarbons but no substantial amount of unsaturated components.

16 Claims, No Drawings

METHOD OF PROCESSING THERMAL CRACKED BY-PRODUCT OIL

BACKGROUND OF THE INVENTION

1. Field of the Invention

This invention relates to a method of processing a thermal cracked by-product oil containing aromatic hydrocarbon compounds from high-temperature cracking of petroleum hydrocarbons in the presence of an acid catalyst to achieve improvement in the composition of the distillates from the thermal cracked by-product oil, reduction of unsaturated components and production of useful heavy products.

2. Description of the Prior Art

So-called naphtha cracking which represents pyrolysis of various petroleum hydrocarbons such as naphtha at a high temperature of 700° C. or higher to produce basic materials for petrochemical industries such as ethylene and propylene is widely employed. Depending upon the nature of the starting oil to be fed to the cracking apparatus, there are produced 0.5–3.0 parts by weight of by-product oil per one part by weight of ethylene product. A distillate of the by-product oil containing components of a boiling range between 75° C. and 198° C. is so-called cracked gasoline distillate which contains as the principal component aromatic hydrocarbons and from which are recovered or produced via an aromatics extraction step, benzene, toluene, mixed-xylenes, $C_9$-alkyl benzenes, $C_{10}$-alkyl benzenes, and the like.

However, as the distillate contains, in addition to the principal aromatic hydrocarbon component, aliphatic saturated hydrocarbons as well as unsaturated components which are aromatic olefins and a minor amount of other unsaturated hydrocarbons, there is included the removal of unsaturated components as a pretreatment step in the conventional aromatics extraction step in order to avoid adverse results such as clogging of the apparatus due to polymerization of the unsaturated components and deterioration due to contamination of the recovered aromatics.

On the other hand, catalytic reformed gasoline, which is an important aromatics source in petrochemical industries compared to thermal cracked by-product oil, has a very low content of unsaturated components (bromine number of 3.8 or below) and there is little need in the said reformed gasoline for a step of removing unsaturated components as a pretreatment step to the aromatics extraction step.

A method of removing unsaturated components of thermal cracked by-product oil which has been put into practical use on an industrial scale is the selective hydrogenation process. Selective hydrogenation requires complete processing of the unsaturated components while inhibiting conversion of the aromatic components to cyclohexanes and polymerization of styrenes. Thus, there are usually associated with this process difficulties in selecting reaction conditions. For example, there is employed at the first stage, hydrogenation of polymerizable components under moderate conditions in order to prevent polymerization of styrenes, followed by the second stage of complete hydrogenation to remove the unsaturated components. In addition, a large amount of hydrogen is consumed in the selective hydrogenation process. Moreover, the hydrogenation results in conversion of the unsaturated components only to substances of little economic value such as alkyl benzenes and paraffins so that resources useful in chemical industry are not efficiently utilized.

For example, styrene which is a main constituent of the unsaturated components in the aforementioned thermal cracked by-product oil, is converted by the hydrogenation into ethylbenzene. As a result, the ethylbenzene content in the xylene distillate obtained by the aromatics extraction step after hydrogenation processing is increased.

Heretofore, mixed-xylenes which have been obtained on an industrial scale have been separated and purified from aromatics-containing distillates of catalytic reformed oil, of naphtha, thermal cracked by-product oil naphtha, or the like, by such means as solvent extraction, extractive distillation, or the like.

The mixed-xylenes contain as principal components o-xylene, m-xylene, p-xylene, ethylbenzene, and the like, and their industrial application is generally as solvents or chemical raw materials. Whereas their use as solvents is not restricted being independent, upon the composition of xylene isomers therein, for their use as chemical raw materials the particular values of p-xylene and o-xylene in the isomers are important. p-Xylene is a starting material for the production of terephthalic acid which finds much demand as a raw material for the production of synthetic fibers. o-Xylene is a starting material for phthalic acid which is a starting material for plasticizers. On the contrary, m-xylene and ethylbenzene are of such little value that their values are increased by conversion of m-xylene by isomerization into p-xylene and conversion of ethylbenzene by isomerization into xylenes or by dehydrogenation into styrene. However, the isomerization of m-xylene is accompanied by high cost in the isomerization step and the ethylbenzene separated from mixed-xylenes is not economically suitable for the industrial production of styrene.

As shown in Table 1, components of mixed-xylenes are close in boiling point, and isolation of each component with only distillation is difficult.

Table 1

| Component | Boiling point (°C.) | Melting point (°C.) |
|---|---|---|
| Ethylbenzene | 136.19 | −94.98 |
| p-xylene | 138.35 | +13.26 |
| m-xylene | 139.10 | −48.87 |
| o-xylene | 144.41 | −25.18 |

The Industrial process for isolating each component of mixed-xylenes is usually a combination of rectification and a low temperature process. First, ethylbenzene and o-xylene which have different boiling points are separated by rectification. However, as it is impractical to separate m-xylene and p-xylene, these isomers being of narrower difference in boiling point, a low temperature process utilizing the difference in melting point is employed, wherein p-xylene crystallized is separated. In either of these separation steps, much energy is consumed so that mixed-xylenes with a higher content of p-xylene but a lower content of m-xylene and ethylbenzene are desirable.

The above-described considerations are important in particular in the case where aromatic hydrocarbon distillates, that is, cracked gasoline distillate, are used, which is distillated from a by-product of cracking of petroleum hydrocarbons such as naphtha conducted principally to obtain ethylene.

A variety of processes have been proposed in order to overcome the above-cited problems by means, for example, of removal of styrene, the precursor of ethylbenzene, in order to reduce ethylbenzene contained in the xylene distillate, at a stage prior to the hydrogenation process such as separation of styrene by rectification, extractive distillation, or selective adsorption with an absorbent. These processes, however, can hardly be considered the most advantageous because of the little value of the styrene separated thereby.

SUMMARY OF THE INVENTION

Rather than employing such simple means as removal by separation of unsaturated components in thermal cracked by-product oil or hydrogenation of the same, we have found a process by which multiple objects can be achieved such as reduction of unsaturated components, isolation of useful products, and which meets the requirements in the aromatic hydrocarbon industry for the composition of processed aromatic hydrocarbons.

This invention is concerned with a method of processing thermal cracked by-product oil which comprises reacting a distillate from thermal cracked by-product oil principally containing components of a boiling range between 75° C. and 198° C. said distillate being one of the distillates from the cracking of petroleum hydrocarbons at a cracking temperature of 700° C. or higher and containing 5–100 molar percent aromatic olefins based upon the aromatic hydrocarbons excluding the aromatic olefins in the liquid phase in the presence of an acid catalyst under such conditions that the reaction temperature is 0° C.–200° C., the liquid residence time is 0.1 hour to 5 hours, and in the presence of aromatic olefins in the reaction system wherein said aromatic olefins are 5% by weight or lower, to yield a processed distillate containing non-condensed di- and tricyclic aromatic compounds which are reaction products of aromatic olefins with other aromatic hydrocarbons but containing no substantial amount of unsaturated components.

DESCRIPTION OF THE INVENTION

There is provided herein a process for achieving removal of styrene, the ethylbenzene precursor, and simultaneously therewith, the reduction of m-xylene by the alkylation addition of styrene which is contained in the xylene distillate from thermal cracked by-product oil, and in addition, the recovery of the reaction products of styrene and xylenes which are non-condensed polycyclic aromatics useful as synthetic oil. Moreover, it has been made clear that the mixed-xylenes processed according to the method of the present invention are superior in composition for industrial use to the mixed-xylenes with ethylbenzene or its precursor, styrene, removed by separation in another way. The present invention is based on the discovery that there are significant differences in reactivity with styrene and xylene isomers. The practical consequence of such discovery is a superior composition for the processed mixed-xylenes herein.

Description will be made below as to how desirable the composition of mixed-xylenes processed according to the method of the invention is as compared with cases where ethylbenzene, etc., are removed by other methods.

Reactivities of ethylbenzene, o-, m- and p-xylene with styrene in aralkylation are shown below, taking the reaction rate of ethylbenzene with styrene as 1.

Table 2

| Relative reaction rates of xylenes | |
|---|---|
| | Relative reaction rate |
| Ethylbenzene | 1 |
| o-xylene | 40 |
| m-xylene | 110 |
| p-xylene | 2 |

As is apparent from the table above, the reactivity of m-xylene is far greater. It follows that when processing is carried out according to the method of this invention, the styrene to be removed will be subjected selectively to aralkylation addition with m-xylene. This results in reduced content of m-xylene, an industrially useless component in the mixed-xylenes. The Increased content of p-xylene and o-xylene thus produced which are important as starting materials for terephthalic and phthalic acid, respectively, make the mixed-xylenes herein highly valuable as industrial raw materials.

According to the method of the present invention, a high concentration of o-xylene and p-xylene which are useful as raw materials in chemical industry is obtained to such an extent that their combined total proportion is 60.0% by weight or higher. One of the notable features of the invention is that a mixed-xylene very desirable in composition for the production of p-xylene as a raw material for the polyester fiber industry can be recovered.

In general, isolation of each component from mixed-xylene is usually effected by a combination of rectification and a low temperature process wherein ethylbenzene and o-xylene, being different in boiling point, are initially separated by rectification. Then m- and p-xylene which are similar in boiling point, in turn, are separated by crystallization. Therefore, a larger ratio of p-xylene to m-xylene is preferable. By the method of the present invention, in which m-xylene is converted into heavy oil through the selective aralkylation with styrene, improved p/m ratio can also be achieved.

Compositions of the xylene distillate from thermal cracked by-product oil (boiling range from 135° C. to 150° C.) are shown below in Table 3 for distillate which is (1) unprocessed, (2) processed by hydrogenation, (3) minus styrene only and (4) processed according to the method of the present invention. The results provided by the invention will be apparent from Table 3.

Table 3

| (Figures are in % by weight.) | | | | |
|---|---|---|---|---|
| | (1) xylene distillate from thermal cracked by-product oil | (2) Hydrogenation process | (3) Separation of styrene | (4) Method of the invention |
| Ethylbenzene | 9.2 | 39.9 | 13.3 | 21.2 |
| o-xylene | 19.4 | 19.4 | 28.0 | 27.6 |
| m-xylene | 28.0 | 28.0 | 40.4 | 18.8 |
| p-xylene | 12.7 | 12.7 | 18.3 | 32.4 |
| Styrene | 30.07 | 0.0 | 0.0 | 0.0 |
| Total of o/p | 32.1 | 32.1 | 46.3 | 60.0 |
| p-xylene/m-xylene | 0.45 | 0.45 | 0.45 | 1.72 |

The figures in Table 3 under (1) are compositions on the basis of total xylenes ($C_8$-aromatic) in the distillate obtained in a temperature range between 135° C. and 150° C. from a thermal cracked by-product oil taken as 100.

The composition after the processing under (3) in the above table represents values on the assumption that ideal removal of the styrene is feasible. Therefore, actual content of the o- and p-xylenes may be considered lower.

As petroleum hydrocarbons which can be used in the present invention are included crude oil, heavy oil, naphtha, kerosene, LPG, butane and a variety of other petroleum hydrocarbons. In consideration of its properties, the thermal cracked by-product oil from naphtha cracking which is aimed at production of ethylene is preferable because of its readily meeting the objects of the invention.

There is no limitation to the method of cracking and a variety of conventional cracking procedures carried out at a temperature of 700° C. or above, for example, using a tubular cracking furnace or a hot medium cracking, can advantageously be employed.

Among the thermal cracked by-product oils thus obtained and which can be used herein is a distillate principally containing components of a boiling range between 75° C. and 198° C. and containing a ratio of 5-100 molar percent aromatic olefins to non-olefinic aromatic hydrocarbons.

If the distillate principally contains components of a boiling range between 75° C. and 198° C., it may also contain a by-product oil beyond the boiling range between 75° C. and 198° C. However, the process should appropriately be conducted in careful consideration of the effects, such as below mentioned, of higher-boiling and lower-boiling components.

Distillates of a boiling range higher than the above-cited are not desirable. Properties of thermal cracked by-product oil change significantly in the boiling point region of 200° C. and above Heavy cracked oil of a boiling point above 200° C. adversely affects the method of this invention. Whereas aromatic components of the light cracked oil of a boiling point below 200° C. are monocyclic aromatics consisting of benzene, toluene, xylenes, $C_3$-alkyl benzenes and $C_4$-alkyl benzenes, those of heavy cracked oil of a boiling point above 200° C. are condensed polycyclic aromatics such as naphthalene, alkylnaphthalenes, anthracene and alkylanthracenes. Condensed polycyclic aromatic compounds, which contain a number of alkylation reactive carbon atoms per molecule, are liable to polyalkylation with a result that a large amount of very high-molecular viscous materials are formed and the yield of useful heavy oil is greatly reduced. As an additional disadvantage, many condensed polycyclic aromatics may not be safe due to their toxicity and incorporation of such components in the recovered heavy oil, even if in a minimum amount, is undesirable.

On the other hand, distillates of a boiling point below 75° C. contain higher proportions of dienes such as cyclopentadiene, and were they processed according to the method of the invention, there would occur polymerization reactions of these dienes producing many highly viscous substances which would inhibit progress of the reaction and also greatly reduce the yield of useful heavy oil.

The thermal cracked by-product oil employed according to the present invention varies, depending upon the nature of the starting the petroleum hydrocarbons to be fed to the cracking apparatus and temperature conditions for cracking, and in general consists of a mixture of oil containing from 6 to 10 carbon atoms of varied composition within the range of 5-15% by weight of saturated aliphatic hydrocarbons, 55-85% by weight of aromatic hydrocarbons consisting of benzene and alkylbenzenes, 2-10% by weight of unsaturated aliphatic hydrocarbons, and 2-15% by weight of aromatic olefins. As shown in Table 4 below which sets forth a typical analysis, light cracked oil is a mixture of various compositions.

Table 4

Typical analysis of light cracked oil

| | n-Paraffin | iso-Paraffin | Naphthene | Aromatics | Olefins* | Sub-total |
|---|---|---|---|---|---|---|
| $C_6$ | 2.3 | 1.9 | 5.2 | 36.7 | 2.5 | 48.6 |
| $C_7$ | 0.4 | 0.5 | 0.7 | 22.5 | 0.5 | 24.6 |
| $C_8$ | 0.1 | 0.1 | 0.5 | 11.5 | 6.1 | 18.3 |
| $C_9$ | 0.1 | 0.1 | 0.1 | 4.8 | 2.7 | 7.8 |
| $C_{10}$ | 0.0 | 0.0 | 0.1 | 0.3 | 0.3 | 0.7 |
| Sub-total | 2.9 | 2.6 | 6.6 | 75.8 | 12.1 | 100.0 |

(Figures are in terms of % by weight.)
*Including aromatic olefins.

Components effectively used in the present invention include alkylbenzene aromatic hydrocarbons such as benzene, toluene, xylenes, cumene, propylbenzene, methylethylbenzenes, trimethylbenzenes, diethylbenzenes and tetramethylbenzenes, and olefins which are unsaturated components to be reacted with the former. Olefins in the thermal cracked by-product oil include various mixtures the $C_8$-$C_{10}$ components of which are mainly aromatic olefins such as styrene, methylstyrenes and ethylstyrenes, and the below-$C_8$ components of which consist of aliphatic olefins such as hexenes and heptenes. The thermal cracked by-product oil also contains components that are solid at ordinary temperatures such as durene, which will not cause any difficulty in carrying out the invention as they are usually in solution.

According to the invention, aromatic olefins in the distillate from thermal cracked by-product oil is contained therein at a ratio of 5-100 molar percent on the basis of the aromatic hydrocarbons excluding the aromatic olefins. When it is below 5 molar percent, production of the desired non-condensed di- or tricyclic aromatic compounds which are reaction products of aromatic olefins and aromatic hydrocarbons will not be satisfactory, and almost no effect will be obtained by processing with an acid catalyst.

On the other hand, when content of the aromatic olefins exceeds 100 molar percent, excess aromatic olefins which have not been consumed by the reaction will remain in the processed solution so that the goal of reducing unsaturated components will not be satisfactorily achieved. Also, dimers and trimers of the unsaturated polymers formed by polymerization reaction of the residual aromatic olefins will be incorporated in the heavy product oil causing the deterioration thereof.

According to the method of this invention, the above-mentioned distillate from thermal cracked by-product oil is reacted in the liquid phase in the presence of an acid catalyst under such conditions that the reaction temperature is 0° C.-200° C., the liquid residence time is 0.1 hour-5 hours, in the presence of aromatic olefins in the reaction system wherein said aromatic olefins are 5% by weight or lower to yield a processed distillate containing non-condensed di- and tricyclic aromatic compounds which are reaction products of aromatic olefins with other aromatic hydrocarbons but no substantial amount of unsaturated components.

The amount of unsaturated component contained in said processed distillate is determined by its bromine number, the usual bromine number of said distillate being 1.0 cg/g or be/ow.

The method of the present invention may be carried out either as a batch process or as a continuous process while obtaining the desired results. The processing conditions may vary within the above-cited range depending upon the manner of processing.

The processing conditions will be described below.

The processing according to the invention should be effected in the liquid phase. Vapor-phase reaction will produce thermal polymerization of the aromatic olefins present in the thermal cracked by-product oil thereby reducing yield of the desired heavy product. Therefore, pressure should be applied during the processing sufficient to maintain the thermal cracked by-product oil to be processed in the liquid phase at a temperature range between 0° C. and 200° C. The Necessary pressure may of course vary depending upon the composition of the thermal cracked by-product oil and processing temperature, but is usually in the range of 40 kg/cm$^2$ or below. The pressure may be any one under which the thermal cracked by-product oil to be processed in the reaction system exists in the liquid phase and is not an essential element of the method according to the invention.

The liquid residence time is preferably from 0.1 to 5 hours. With less than 0.1 hour, the reaction of unsaturated components in the thermal cracked by-product oil will not be satisfactorily completed. Contact with the acid catalyst for a period of time longer than 5 hours will cause decomposition of the reaction products to increase the amount of unsaturated components.

Temperature is an important element of the method according to the present invention. Use of a temperature below 0° C. is undesirable because there will then be formed high-molecular tar-like substances by polymerization reaction of highly reactive styrenes contained in the thermal cracked by-product oil. At temperatures exceeding 200° C., thermal decomposition will take place to increase the unsaturated components instead of the objective to decrease the same. The processing temperature may vary depending upon the catalyst employed. With a solid acid catalyst, the temperature is preferably 100° C. or higher, that is, 100° C.–200° C., more preferably 120° C.–180° C. It is preferable in the case of a mineral acid or Friedel-Crafts catalyst to employ a temperature of 100° C. or lower, that is, 0° C.–100° C., more preferably 5° C.–60° C.

As the acid catalyst used in the present invention are preferably mentioned solid acid catalysts, mineral acids, so-called Friedel-Crafts catalysts and the like. For example, acid clay minerals such as acid clay, active clay and silica-alumina, hydrogen fluoride, sulfuric acid, phosphoric acid, aluminum chloride, tin chlorides, boron fluoride, aluminium bromide, boron chloride, ferric chloride, titanium bromide, titanium chloride, zinc chloride, their etherates or phenolates, and the like may be employed. However, when removal of styrene, the precursor of ethylbenzene, is intended from a distillate of a boiling range from 130° C. to 150° C. by means of selective alkylation addition by the use of the difference in reactivity between the xylene isomers contained in the same, a solid acid catalyst and sulfuric acid are more preferred catalysts.

In the case when too much of said catalysts is employed, undesirable decomposition of the products occurs. Therefore, the usual amount of catalyst employed is 30% or less by weight of the distillate to be processed.

It is necessary in order to obtain a heavy product principally containing reaction products between aromatic olefins and aromatic hydrocarbons in a high yield to limit the aromatic olefin components present in the process system to 5% by weight at maximum. This is one of the important elements of the method according to the present invention whether the type of the reaction is batch process or continuous process.

When the concentration of aromatic olefins in the reaction system exceeds 5% by weight, polymerization of styrene which is especially reactive among the unsaturated components will predominate thereby adversely affecting the yield of synthetic oil. Especially in the case of a continuous process, the reaction heat will increase the temperature of the catalyst layer causing thermal decomposition locally at high temperature sites. As shown by the typical analysis in Table 1, ordinary thermal cracked oil contains 5% by weight or more of unsaturated components in total. It is therefore necessary to adjust the concentration of aromatic olefins in the reaction system by recycling the distillate from the reaction process or by recycling the light distillate after recovery by distillation of the heavy reaction product. Alternatively, one or more monocyclic aromatic hydrocarbons (excluding aromatic olefins) present in the original distillate from thermal cracked by-product oil or in the processed distillate may be added to the reaction system. For instance, the distillate may be diluted at the early stage of the reaction with xylenes, followed by use of the light oil recovered from the reaction product.

According to the method of the invention, both aromatic and aliphatic olefins which are unsaturated components in the thermal cracked by-product oil are mainly employed for the alkylation reaction with aromatic hydrocarbons. Processing by the reaction under the above-cited conditions results in substantially complete consumption of the unsaturated components as indicated by a decrease of the initial bromine value of 30 to 0.3 or below, thereby achieving the object of removing unsaturated components.

Therefore, the processed distillate may be employed as is in the aromatic hydrocarbon preparation step such as an aromatic hydrocarbon extraction step without passing through the unsaturated component removal step such as a hydrogenation process which consumes a large amount of hydrogen. Of course, an additional hydrogenation step may be optionally carried out in order to perform complete removal of a minimum amount of the unsaturated component.

Moreover, the unsaturated components consumed by the reaction can be recovered in the form of useful heavy product.

The method of the present invention is directed not only to substantial removal of unsaturated components in cracked oil but also to production of industrially useful products. The heavy reaction product obtained according to the invention is an alkylated product mixture between alkylbenzenes contained in thermal cracked by-product oil such as benzene, toluene, xylenes, ethylbenzene, C$_9$ aromatics and C$_{10}$ aromatics and aromatic olefins such as styrene, α-methylstyrene and vinyltoluenes and a variety of aliphatic olefins. Composition of the recovered heavy oil varies according to the nature of the cracked oil to be processed, and as the principal components are mentioned alkylbenzenes, non-condensed dicyclic aromatics such as diphenylalkanes and non-condensed tricyclic aromatics. The alkylbenzenes are alkylated products of aromatic hydrocarbons and aliphatic olefins contained in cracked oil which are monocyclic polyalkylbenzenes of $C_nH_{2n-6}$ wherein n is between 12 and 20 as determined by mass spectroscopy. The diphenylalkanes are alkylated products of aromatic hydrocarbons and aromatic olefins such as styrene contained in thermal cracked by-product oil which are non-condensed diphenyl compounds of $C_nH_{2n-14}$ wherein n is between 14 and 20 as determined by mass spectroscopy. Heavier reaction products have the formula $C_nH_{2n-22}$ wherein n is between 22 and 30 which is a distillate mainly composed of non-condensed tricyclic aromatic hydrocarbons from the alkylation addition of two moles of styrene to one mole of aromatics in the cracked oil.

When xylene distillate contained in thermal cracked by-product oil is processed according to the method of the present invention, non-condensed di- and tricyclic aromatic hydrocarbons which are industrially useful heavy reaction products are obtained and a high concentration of industrially useful o-xylene and p-xylene in the mixed-xylenes can be achieved as well.

According to mass spectroscopy, di- and tricyclic aromatic compound which are obtained from the said processing of xylene distillate are aromatic hydrocarbons principally comprising xylyphenylethane (m/e=210, $C_{16}H_{18}$) and a triphenyl compound (m/e=314, $C_{24}H_{26}$) respectively.

On the other hand, reaction products of so-called thermal cracked gasoline contain reaction products with aliphatic olefins and aromatic hydrocarbons as well.

The boiling points of heavy products contained in the distillate processed according to the method of this invention are greatly different from those of the mixed-xylenes.

Therefore, separation of di- and tricyclic aromatic compound can be easily effected by ordinary distillation. However, said heavy products are preferably distillated at reduced pressure to avoid thermal decomposition because of their high boiling temperatures at atmospheric pressure.

These heavy reaction products, either as they exist in mixture or after separation by distillation as desired possess excellent compatibility, lubricity, heat resistance and electric properties and are suitable for wide use as plasticizers, high-boiling solvents, heat transfer media, electric insulation oil, working oil, and the like.

Moreover, as styrene which is the main component of the aromatic olefins is recovered as a useful component, the increase of ethylbenzene which is associated with prior art hydrogenation processes is no longer observed so that the effective use of aromatic hydrocarbons, especially of xylene is increased.

DESCRIPTION OF THE PREFERRED EMBODIMENTS

EXAMPLE 1

Naphtha cracking by-product oil with a bromine number of 30.6 cg/g, a boiling range between 68° C. and 175° C. (content of the component with a boiling range between 75° C. and 175° C. being 95.8% by weight), 12.1% by weight of aliphatic saturated component, 75.8% by weight of aromatics and 12.1% by weight of olefins (containing 91% of aromatic olefins), acid clay as the acid catalyst, and xylenes as the diluent at the initial stage of reaction were employed. (The use of xylenes in this example is for dilution of the aromatic olefins at the initial stage of reaction. Therefore, when the process of the invention is repeated, use of the recovered light oil from distillation of the processed mixture will be satisfactory.)

In an autoclave 15 l. in volume equipped with a stirrer, thermometer and heating device are placed 1 kg. of the above-cited xylenes and 200 g. of acid clay, and pressure is applied with nitrogen to 30 kg./cm$^2$G. While heating to a temperature of 100° C., 600 g. of the above-cited cracking by-product oil (concentration of the aromatic olefins in the reaction system being 4.5% by weight in this case) is added under stirring, and the mixture is reacted for 30 min. After the reaction, a 10-g. aliquot is taken and measured for bromine number, which is 0.5 or lower. Then, an additional 600 g. of the aforementioned cracking by-product oil is added, and the reaction is repeated 10 times in total with 6 kg. of the cracking by-product oil added.

After cooling, the clay is separated by filtration. There was obtained 6.75 kg. of the processed cracking by-product oil. The product had a bromine number of 0.37 cg/g with a ratio of unsaturation removal of 98.8%.

Then, separation was made by distillation under ordinary pressure up to a distillation temperature of 150° C. and under reduced pressure for heavier distillates.

| Distillate | Results of the distillation | | | |
|---|---|---|---|---|
| | % by weight | B.P. °C./mm.Hg | Br number cg/g | |
| 1 | 32.0 | 65°–180° C./760 | 0.29 | Specific gravity 15/4° C. 0.84 |
| 2 | 14.2 | 100°–168° C./3 | 0.37 | Specific gravity 15/4° C. 0.98 |
| 3 | 3.1 | 190°–230° C./3 | 1.42 | Specific gravity 50/4° C. 1.01 |
| 4 | 0.7 | Residue | — | Resinous mass |

| (1) Analysis of recovered distillate No. 1 | | |
|---|---|---|
| Bromine number cg/g | Naphtha cracking By-product oil 30.6 | Distillate No. 1 processed according to the invention 0.29 |
| Analysis | % by wt. | % by wt. |
| Saturated aliphalic | 12.1 | 15.9 |
| Aromatic | 75.8 | 83.8 |
| Olefinic | 12.1 | 0.3 |

The above results show that the degree of unsaturation for recovered distillate No. 1 which is a light oil recovered from the distillation following processing by the method of the invention is greatly improved. For completely removing unsaturated components by hydrogenation of the same, hydrogen consumed by the hydrogenation will be much reduced being 1% or below as compared with the consumption of hydrogen for the unprocessed by-product oil.

Although two-stage hydrogenation is carried out as a conventional pretreatment for the aromatics extraction step, hydrogenation of polymerizable components under moderate conditions at the first stage and complete hydrogenation to remove unsaturated components at the second stage, the first stage hydrogenation can be omitted for recovered distillate No. 1 processed by the method of the invention.

| (2) Analysis of recovered distillates No. 2 and No. 3 | | |
|---|---|---|
| Type | No. 2 | No. 3 |
| $CnH_{2n+2}$ (Paraffins) | 0.3 wt. % | 0.1 wt. % |
| $CnH_{2n}$ (Olefins) | 0.4 | 2.8 |
| $CnH_{2n-6}$ (n = 15-22) (Alkylbenzenes) | 18.3 | 4.2 |
| $CnH_{2n-14}$ (n = 15-20) (Diphenylalkanes) | 80.9 | 4.3 |
| $CnH_{2n-22}$ (n = 23-31) (Triphenyls) | 0.1 | 88.1 |

EXAMPLE 2

There were employed the naphtha cracking by-product oil used in Example 1, 90% sulfuric acid as the acid catalyst and the light distillate recovered in Example 1 as the diluent at the initial stage of reaction.

In a reaction vessel 15 l. in volume equipped with a stirrer and thermometer are placed 1 kg. of the diluent and 200 g. of 90% sulfuric acid, and the mixture is cooled to a temperature of 5° C. or below. Then, 600 g. of the above-mentioned cracking by-product oil is added with stirring, and the mixture is reacted for 30 min. The concentration of aromatic olefins was 45% by weight. After addition of the by-product oil cooling is required so as to keep the temperature increase due to the reaction heat within 10° C. After the reaction, a 10-g. aliquot was taken and measured for bromine number, which was 0.08. Then, reaction with an additional 600 g. of the aforementioned by-product oil added is repeated with 6 kg. of the cracking by-product oil in total added.

After completion of the reaction, the sulfuric acid is separated by settlement, and the processed solution is neutralized by the addition of 1 l. of 5% aqueous solution of sodium hydroxide. After the neutralization, washing with water is carried out until the wash water is neutral (pH 6.8-7.2). There is obtained 6.65 kg. of a neutralized and washed solution, which has a bromine number of 0.07 with a ratio of unsaturation removal of 99.8%.

Then, separation was effected by distillation under ordinary pressure for light distillates up to 150° C. and under reduced pressure for heavier distillates.

| Results of the distillation | | | | |
|---|---|---|---|---|
| Distillate | % by wt. | B.P. °C./mm.Hg | Br number cg/g | Specific gravity 15/4° C. |
| 1 | 80.8 | 65-180/760 | 0.02 | 0.84 |
| 2 | 15.7 | 100-168/3 | 0.21 | 0.98 |
| 3 | 2.9 | 190-230/3 | 1.17 | 1.01 |
| 4 | 0.6 | Residue | — | Resinous mass |

| Analysis of recovered distillate No. 1 | | |
|---|---|---|
| Bromine number cg/g | Naphtha cracking by-product oil 30.6 | Distillate No.1 processed by the invention 0.02 |
| Analysis | wt.% | wt.% |
| Saturated aliphatic | 12.1 | 15.3 |
| Aromatic | 75.8 | 84.7 |
| Olefinic | 12.1 | 0.1 or below |

Said recovered distillate obtained in this example has a bromine number of 0.02, which evidently indicates that all the treatment prior to hydrogenation as described in Example 1 can be omitted.

| Analysis of recovered distillates No.2 and No.3 (The formulae of the compound type and the range of n are the same as in Example 1.) | | |
|---|---|---|
| Type | No.2 | No.3 |
| Paraffins | 0.3 wt. % | 0.1 wt. % |
| Olefins | 0.3 | 2.3 |
| Alkylbenzenes | 16.7 | 3.7 |
| Diphenylalkanes | 82.6 | 4.6 |
| Triphenyls | 0.1 | 89.3 |

EXAMPLE 3

Distillate of the boiling range between 135° C. and 148° C. which is a xylene distillate was separated by distillation from cracking by-product oil rich in aromatics by-produced in a naphtha raw material cracking step. Composition of the xylene distillate is shown below.

| Non-aromatics | 3.7% by weight | |
|---|---|---|
| Toluene | 0.1 | |
| Ethylbenzene | 8.8 | 13.2 |
| o-xylene | 18.6 | 28.0 |
| m-xylene | 26.9 | 40.5 |
| p-xylene | 12.2 | 18.3 |
| Styrene | 29.5 | 100.0 |
| Cumene | 0.2 | |
| | 100.0 | |

As the diluent at the initial stage of reaction, a formulated xylene was used which contained 13.2% by weight of ethylbenzene, 28.0% by weight of o-xylene, 40.5% by weight of m-xylene, and 18.3% by weight of p-xylene. (The formulated xylene is used in this example as a diluent for styrene at the initial stage of reaction. Therefore, when the reaction of the invention is repeated, used of recovered xylenes thus processed will be satisfactory.)

In a reaction vessel 10 l. in volume equipped with a stirrer and thermometer are placed 400 g. of the formulated xylene and 200 g. of 90% sulfuric acid. The mixture is cooled to a temperature of 5° C. While stirring, the above-mentioned xylene distillate is added dropwise at a rate of 100-200 ml./min. After completion of the addition, stirring is continued for 10-15 min. and temperature increase due to the reaction heat is ceased. When the temperature again dropped to 5°-7° C. further addition of the aforementioned xylene distillate is made. In order to maintain the concentration of styrene in the reaction system at 5% or below, the addition is carried out in such a manner that five 65-g. portions, five 120-g. portions, five 220-g. portions, five 410-g. portions and five 760-g. portions, that is, 7875 g. in total, are reacted. In this case, the concentration of styrene varies within the range between 2.7 and 4.1%.

After completion of the reaction, the sulfuric acid is separated by settlement and the reaction mixture is neutralized with 5% aqueous solution of sodium hydroxide. Washing with water is carried out until the wash water is neutral (pH 6.8-7.2).

The unreacted processed xylene is separated under ordinary pressure up to a distilling temperature of 150°

C. The by-product heavy oil is recovered under reduced pressure.

Structural formulae were determined by gas chromatographic analysis for the processed xylene thus recovered, and by mass spectroscopy and IR spectroscopy for the by-product heavy oil. The results are shown in Table 5.

The heavy by-product oil obtained in this example is an aralkylated product between xylenes and styrene, which is composed of two distillates, one obtained under reduced pressure (3 mm.Hg) at 135°–150° C. and the other at 180°–230° C. The first distillate of a boiling range between 135° C. and 150° C. is a styrenated xylene mainly composed of 1-metaxylyl-1-phenylethane. The second distillate of a boiling range between 180° C. and 230° C. was a distillate mainly composed of di-clay is separated by filtration, and separation is effected by distillation. The results are shown in Table 5.

COMPARATIVE EXAMPLE 1

The procedures were the same as in Example 3, except that 2×300 g., 2×1000 g. and 2×1500 g., that is, 6800 g. in total, was reacted so that the concentration of styrene in the reaction system exceeded 5%. The styrene concentration in this case varied within the range between 6.1 and 12.6%. The results are shown in Table 5.

COMPARATIVE EXAMPLE 2

The same procedures as in Example 3 were employed. As the catalyst was used 25 g. of aluminum chloride. The results are shown in Table 5.

Table 5

| Example | Example 3 | Example 4 | Comparative Example 1 | Comparative Example 2 |
|---|---|---|---|---|
| Results of the separation by distillation | | | | |
| Boiling point °C./mm.Hg | wt. % | wt. % | wt. % | wt. % |
| (1) 135–150/760 | 49.7 | 52.0 | 60.3 | 67.4 |
| (2) 130–150/3 | 38.5 | 32.4 | 16.0 | 3.0 |
| (3) 180–230/3 | 8.4 | 10.3 | 15.1 | 4.5 |
| Residue | 3.4 | 5.3 | 8.6 | 25.1 |
| Conversion ratio of styrene to the residue mol. % | 11.5 | 17.9 | 29.2 | 85.1 |
| Analysis of processed xylene distillate (1) | | | | |
| | Value for gas chromatography (wt. %) | | | |
| Ethylbenzene | 19.9 (21.2) | 18.3 (19.3) | 15.5 (17.5) | 14.1 (15.0) |
| o-xylene | 26.0 (27.6) | 25.1 (26.6) | 27.2 (28.8) | 26.5 (28.3) |
| m-xylene | 17.7 (18.8) | 20.2 (21.4) | 19.1 (30.0) | 34.7 (37.0) |
| p-xylene | 30.5 (32.4) | 30.9 (32.7) | 31.6 (23.7) | 18.4 (19.7) |
| Styrene | 0.0 (0.0) | 0.0 (0.0) | 0.0 (0.0) | 0.0 (0.0) |
| | (100.0) | (100.0) | (100.0) | (100.0) |
| Non-aromatics | 5.7 | 5.3 | 5.4 | 6.1 |
| Toluene | 0.1 | 0.1 | 0.1 | 0.1 |
| Cumene | 0.1 | 0.1 | 0.1 | 0.1 |
| | 100.0 | 100.0 | 100.0 | 100.0 |
| Total of o + p | (60.0) | (59.3) | (52.5) | (48.0) |
| p-xylene/m-xylene | 1.72 | 1.53 | 0.79 | 0.53 |
| Bromine number cg/g | 0.03 | 0.06 | 1.13 | 1.89 |
| Analysis of distillate (2) | | | | |
| Mass spectroscopy m/e | 210 | 210 | 210 & 208 | 210 & 208 |
| Bromine number cg/g | 0.12 | 0.36 | 1.27 | 3.43 |
| Distillate (3) | | | | |
| Mass spectroscopy m/e | 314 | 314 | 314 & 312 | 314 & 312 |
| Bromine number | 1.08 | 1.77 | 3.46 | 17.8 |

*Figures in the bracket indicate proportion in the aromatics.

styrenated xylene.

EXAMPLE 4

The cracking xylene distillates used in Example 3 were employed. As the diluent at the initial stage of reaction was employed the recovered processed xylene obtained in Example 3.

In a reaction vessel 10 l. in volume equipped with a stirrer and thermometer are placed 1000 g. of the aforementioned recovered processed xylene and 250 g. of acid clay. The mixture is then heated to the refluxing temperature.

Addition of cracking xylene distillates is carried out at 100–200 ml./min., portionwise in the same way as in Example 1 by 5×170 g., 5×300 g., 5×500 g. and 2×900 g. After completion of the reaction, the acid

EXAMPLE 5

Processing of cracked oil xylene distillate.

In a reaction vessel are placed 100 g. of the processed xylene recovered according to Example 2 as the diluent at the initial stage of reaction and 100 g. of 90% sulfuric acid. The mixture is cooled in the same way as in Example 2. At a temperature from 5° C. to 10° C., 2000 g. of the xylene distillate obtained in Example 1 is added dropwise. Other procedures are the same as in Example 1. Results are shown in Table 6.

EXAMPLE 6

Processing of cracked oil xylene distillate.

As the processing catalyst was employed 100 g. of active clay (Oleonite-236 manufactured by Mizusawa Kagaku Kogyo K.K.). In a reaction vessel 3 l. in volume equipped with a reflux cooler and stirrer are placed 100 g. of the active clay and 100 g. of the xylene processed according to Example 2. The mixture is heated to the refluxing temperature. Under heating to maintain reflux, 2000 g. of the xylene obtained in Example 1 was added dropwise. After completion of the addition, the reaction mixture is cooled, the active clay filtered, and the filtrate subjected to distillation. Results are shown in Table 6.

Table 6

| Example | 3 | 4 |
|---|---|---|
| Processed xylene distillate | | |
| Recovery | 930 g. | 950 g. |
| Ethylbenzene | 16.2% (17.8) | 16.4% (17.8) |
| p-xylene | 35.4% (38.8) | 35.5% (38.6) |
| m-xylene | 24.0% (26.3) | 25.7% (27.9) |
| o-xylene | 15.7% (17.1) | 14.4% (15.7) |
| | (100.0) | (100.0) |
| Aromatics | 8.5% | 7.8% |
| Toluene | 0.1% | 0.1% |
| Cumene | 0.1% | 0.1% |
| | 100.0 | 100.0 |
| o + p in the xylenes | (55.9) | (54.3) |
| First distillate | | |
| Distillation temperature | 134°–150° C. | 135°–150° C. |
| Yield | 892 g. | 822 g. |
| Second distillate | | |
| Distillation temperature | 180°–230° C. | 180°–230° C. |
| Yield | 160 g. | 183 g. |
| Yield of styrene | 95.1% | 92.8% |

*Figures in brackets indicate proportion in the aromatics.

COMPARATIVE EXAMPLE 3

The procedures were the same in Example 1 except that addition of 1.2 kg. portion of cracking by-product oil was repeated 5 times instead of the 600 g. portion in Example 1. The aromatic olefin concentration was 9% by weight.

Bromine number of the processed solution was 9.7 with a ratio of unsaturation removal as low as 68%.

| Results of the distillation | | | |
|---|---|---|---|
| Distillate recovered | % by weight | B.P.°C./mm.Hg | Bromine number cg/g |
| 1 | 87.4 | 65–180/760 | 8.6 |
| 2 | 6.1 | 100–168/3 | 3.4 |
| 3 | 3.1 | 190–230/3 | 4.7 |
| 4 | 3.4 | Residue | — |

| Analysis of recovered distillate No.1 | | |
|---|---|---|
| | Naphtha cracking by-product oil | Comparative Example 3 |
| Bromine number cg/g | 30.6 | 8.6 |
| Analysis | wt.% | wt.% |
| Saturated aliphatic | 12.1 | 14.0 |
| Aromatic | 75.8 | 80.3 |
| Olefinic | 12.1 | 3.7 |

When the aromatic olefin concentration in the reaction system is high as 9% as in this comparative example, the ratio of unsaturation removal is low, the resinuous products are increased and yield of useful heavy by-product oil, especially recovered distillate 2, is decreased. Accordingly, the procedure of this comparative example is not preferred.

We claim:

1. Method of improving thermal cracked by-product oil to remove undesirable unsaturates and recover an improved processed distillate which comprises reacting a distillate from a thermal cracked by-product oil principally containing components of a boiling range between 75° C. and 198° C., said distillate being selected from one of the distillates from the thermal cracking of petroleum hydrocarbons at a temperature of 700° C. or higher, and containing a ratio of 5–100 molar percent undesirable aromatic olefins to non-olefinic aromatic hydrocarbons, in liquid phase in the presence of an acid catalyst under such conditions that the reaction temperature is 0° C.–200° C., the liquid residence time is 0.1 hour–5 hours and wherein the content of said aromatic olefins in the reaction system is maintained at 5% by weight or less, to yield a processed distillate containing non-condensed di- and tricyclic aromatic compounds which are reaction products of said aromatic olefins with a portion of said non-olefinic aromatic hydrocarbons and without substantial reaction with other unsaturated components and distilling said processed distillate to get said improved processed distillate and a heavy reaction product oil.

2. Method or processing thermal cracked by-product oil according to claim 1 wherein a diluent is added to the reaction system so as to maintain the content of the aromatic olefins in the reaction system at 5% by weight or less.

3. Method of processing thermal cracked by-product oil according to claim 2 wherein the diluent is one or a mixture thereof selected from the group consisting of:
   (i) said processed distillate;
   (ii) one or more non-olefinic monocyclic aromatic hydrocarbons which are the same sort of non-olefinic aromatics present in the distillates from the thermal cracked by-product oil or said processed distillate; and,
   (iii) a light oil recovered from said processed distillate by separation of the heavy reaction product.

4. Method of processing thermal cracked by-product oil according to claim 1 wherein said distillate from the cracked by-product oil is a xylene distillate within a boiling range between 130° C. and 150° C. and reduction of the m-xylene and styrene contents in said xylene distillate is achieved by aralkylation reaction by which noncondenced di- and tricyclic aromatic hydrocarbons are produced between xylenes and styrene in said xylene distillate.

5. Method of processing thermal cracked by-product oil according to claim 1 wherein said cracked oil contains 5–15% by weight of saturated aliphatic hydrocarbons, 55–85% by weight of aromatic hydrocarbons, 2–10% by weight of unsaturated aliphatic hydrocarbons and 2–15% by weight of aromatic olefins.

6. Method of processing thermal cracked by-product oil according to claim 1 wherein said acid catalyst is selected from the group comprising solid acid catalysts, mineral acids and Friedel-Crafts catalysts.

7. Method of processing thermal cracked by-product oil according to claim 4 wherein said acid catalyst is selected from the group comprising solid acid catalysts and mineral acids.

8. Method of processing thermal cracked by-product oil according to claim 6 wherein said solid acid catalyst is selected from the group comprising acid clay, active clay and silica-alumina.

9. Method of processing thermal cracked by-product oil according to claim 6 wherein said mineral acid is selected from the group comprising hydrogen fluoride, sulfuric acid and phosphoric acid.

10. Method of processing thermal cracked by-product oil according to claim 6 wherein said Friedel-Crafts catalyst is selected from the group comprising aluminum chloride, aluminum bromide, boron fluoride, boron chloride, ferric chloride, titanium bromide, titanium chloride, tin chloride, zinc chloride and their etherate or phenolate.

11. Method of processing thermal cracked by-product oil according to claim 7 wherein said solid acid catalyst is selected from the group comprising acid clay, active clay and silica-alumina.

12. Method of processing thermal cracked by-product oil according to claim 7 wherein said mineral acid is selected from the group comprising hydrogen fluoride, sulfuric acid and phosphoric acid.

13. Method of processing thermal cracked by-product oil according to claim 1 wherein said non-condensed di- and tricyclic aromatic compounds are separated from the said processed distillate.

14. Method of processing thermal cracked by-product oil according to claim 4 wherein said non-condensed di- and tricyclic aromatic compounds which are reaction product with xylenes and styrene are separated from the said processed distillate.

15. Method of processing thermal cracked by-product oil according to claim 1 wherein said non-condensed dicyclic aromatic hydrocarbons are non-condensed diphenyl hydrocarbons, $C_nH_{2n-14}$; n=14–20 and said non-condensed tricylic aromatic hydrocarbons are non-condensed triphenyl hydrocarbons, $C_nH_{2n-22}$; n=22–30.

16. Method of processing thermal cracked by-product oil according to claim 4 wherein said non-condensed dicyclic aromatic hydrocarbons are xylylphenylethane—$C_{16}H_{18}$ and non-condensed tricyclic aromatic hydrocarbons are triphenyl hydrocarbons—$C_{24}H_{26}$.

* * * * *